(12) United States Patent
Swanson

(10) Patent No.: US 8,518,038 B2
(45) Date of Patent: *Aug. 27, 2013

(54) ELECTROPHYSIOLOGY ELECTRODE HAVING MULTIPLE POWER CONNECTIONS AND ELECTROPHYSIOLOGY DEVICES INCLUDING THE SAME

(75) Inventor: David K. Swanson, Campbell, CA (US)

(73) Assignee: Endoscopic Technologies, Inc. (ESTECH), San Ramon, CA (US)

( * ) Notice: Subject to any disclaimer, the term of this patent is extended or adjusted under 35 U.S.C. 154(b) by 896 days.

This patent is subject to a terminal disclaimer.

(21) Appl. No.: 12/688,618

(22) Filed: Jan. 15, 2010

(65) Prior Publication Data

US 2010/0121322 A1    May 13, 2010

Related U.S. Application Data

(63) Continuation of application No. 10/255,025, filed on Sep. 24, 2002, now Pat. No. 7,674,258.

(51) Int. Cl.
A61B 18/14 (2006.01)

(52) U.S. Cl.
USPC ............................. 606/52; 606/41; 606/49

(58) Field of Classification Search
USPC .............. 606/32–35, 41, 42, 45–52
See application file for complete search history.

(56) References Cited

U.S. PATENT DOCUMENTS

| | | | |
|---|---|---|---|
| 4,685,459 A | 8/1987 | Koch |
| 4,834,090 A | 5/1989 | Moore |
| 5,190,541 A | 3/1993 | Abele |
| 5,250,072 A | 10/1993 | Jain |
| 5,300,087 A | 4/1994 | Knoepfler |
| 5,364,395 A | 11/1994 | West, Jr. |
| 5,443,463 A | 8/1995 | Stern |
| 5,456,682 A | 10/1995 | Edwards et al. |
| 5,484,435 A | 1/1996 | Fleenor |
| 5,496,312 A | 3/1996 | Klicek |
| 5,562,720 A | 10/1996 | Stern |
| 5,575,810 A | 11/1996 | Swanson et al. |
| 5,582,609 A | 12/1996 | Swanson et al. |
| 5,673,695 A | 10/1997 | McGee |
| 5,697,536 A | 12/1997 | Eggers |
| 5,702,386 A | 12/1997 | Stern |
| 5,755,715 A | 5/1998 | Stern et al. |
| 5,797,905 A | 8/1998 | Fleischman et al. |
| 5,837,001 A | 11/1998 | Mackey |
| 5,871,523 A | 2/1999 | Fleischman |
| 5,904,681 A | 5/1999 | West |
| 5,935,079 A | 8/1999 | Swanson |
| 5,954,686 A | 9/1999 | Garito |
| 5,961,513 A | 10/1999 | Swanson et al. |
| 5,980,519 A | 11/1999 | Hahnen et al. |
| 6,050,996 A | 4/2000 | Schmaltz et al. |

(Continued)

FOREIGN PATENT DOCUMENTS

EP    0856291 A2    8/1998
EP    0694291 A1    10/2001

(Continued)

*Primary Examiner* — Michael Peffley
(74) *Attorney, Agent, or Firm* — Kikpatrick Townsend & Stockton LLP

(57) ABSTRACT

An electrophysiology electrode having multiple power connections and electrophysiology devices including the same.

20 Claims, 9 Drawing Sheets

(56) References Cited

U.S. PATENT DOCUMENTS

| | | | |
|---|---|---|---|
| 6,056,747 A * | 5/2000 | Saadat et al. ............... 606/50 |
| 6,063,078 A | 5/2000 | Wittkampf |
| 6,096,037 A | 8/2000 | Mulier et al. |
| 6,115,626 A | 9/2000 | Whayne |
| 6,142,994 A | 11/2000 | Swanson et al. |
| 6,146,379 A | 11/2000 | Fleischman |
| 6,162,220 A | 12/2000 | Nezhat |
| 6,171,305 B1 | 1/2001 | Sherman |
| 6,183,468 B1 | 2/2001 | Swanson |
| 6,190,381 B1 | 2/2001 | Olsen et al. |
| 6,200,314 B1 | 3/2001 | Sherman |
| 6,224,593 B1 | 5/2001 | Ryan |
| 6,237,604 B1 | 5/2001 | Burnside |
| 6,245,068 B1 | 6/2001 | Olson et al. |
| 6,273,887 B1 | 8/2001 | Yamauchi et al. |
| 6,277,117 B1 | 8/2001 | Tetzlaff |
| 6,312,425 B1 * | 11/2001 | Simpson et al. ............. 606/32 |
| 6,319,249 B1 | 11/2001 | Tollner |
| 6,346,104 B2 | 2/2002 | Daly |
| 6,383,183 B1 | 5/2002 | Sekino et al. |
| 6,421,556 B2 | 7/2002 | Swanson |
| 6,440,130 B1 | 8/2002 | Mulier |
| 6,464,700 B1 | 10/2002 | Koblish et al. |
| 6,471,699 B1 | 10/2002 | Fleischman et al. |
| 6,485,487 B1 | 11/2002 | Sherman |
| 6,488,680 B1 | 12/2002 | Francischelli et al. |
| 6,494,880 B1 | 12/2002 | Swanson |
| 6,533,784 B2 | 3/2003 | Truckai |
| 6,558,408 B1 | 5/2003 | Fogarty et al. |
| 6,616,661 B2 | 9/2003 | Wellman et al. |
| 6,638,274 B2 | 10/2003 | Yamamoto |
| 6,652,514 B2 | 11/2003 | Ellman |
| 6,692,491 B1 | 2/2004 | Phan |
| 6,699,240 B2 | 3/2004 | Francischelli |
| 6,771,996 B2 | 8/2004 | Bowe |
| 6,807,968 B2 | 10/2004 | Francischelli et al. |
| 6,889,694 B2 | 5/2005 | Hooven |
| 7,115,122 B1 | 10/2006 | Swanson |
| 7,674,258 B2 | 3/2010 | Swanson |
| 7,753,908 B2 | 7/2010 | Swanson |
| 7,785,324 B2 | 8/2010 | Eberl |
| 2001/0001314 A1 | 5/2001 | Davison et al. |
| 2001/0025177 A1 | 9/2001 | Woloszko |
| 2002/0026187 A1 | 2/2002 | Swanson |
| 2002/0099428 A1 | 7/2002 | Kaufman |
| 2002/0120267 A1 | 8/2002 | Phan |
| 2003/0097126 A1 | 5/2003 | Woloszko et al. |
| 2003/0158549 A1 | 8/2003 | Swanson |
| 2003/0212444 A1 | 11/2003 | Truckai |
| 2004/0059325 A1 | 3/2004 | Swanson |
| 2005/0019653 A1 | 1/2005 | Dahlberg |
| 2005/0203499 A1 | 9/2005 | Pendekanti |
| 2006/0047277 A1 | 3/2006 | Eberl |

FOREIGN PATENT DOCUMENTS

| | | |
|---|---|---|
| EP | 1557129 A1 | 7/2005 |
| JP | 11-332880 A2 | 12/1999 |
| JP | 2000-107196 A2 | 4/2000 |
| JP | 2000-201945 A2 | 7/2000 |
| JP | 2001-190564 A2 | 7/2001 |
| WO | WO 99/56648 A1 | 11/1999 |
| WO | WO 01/72234 A1 | 10/2001 |

\* cited by examiner

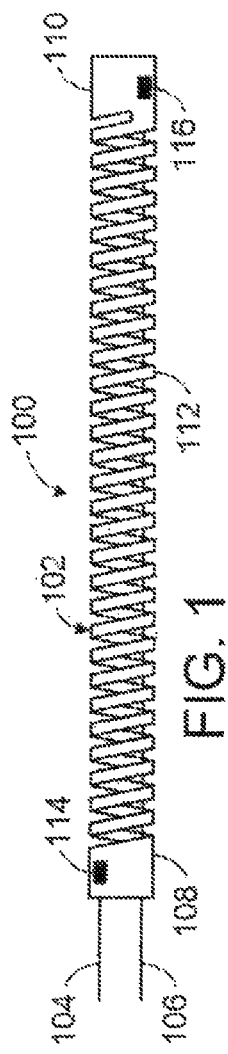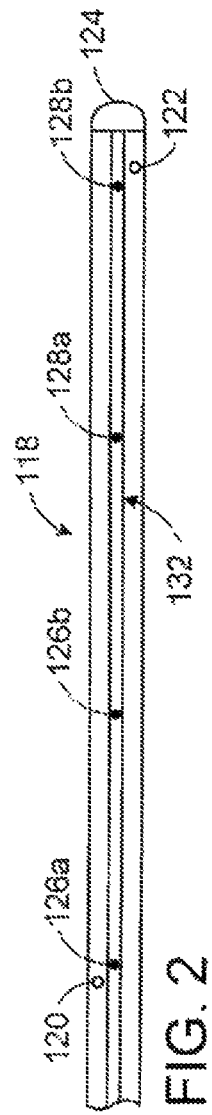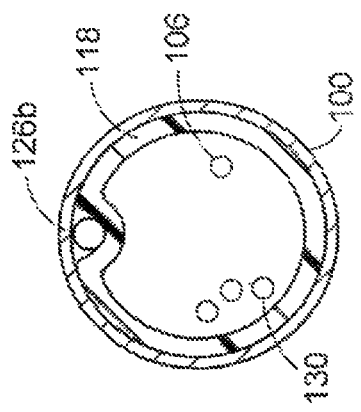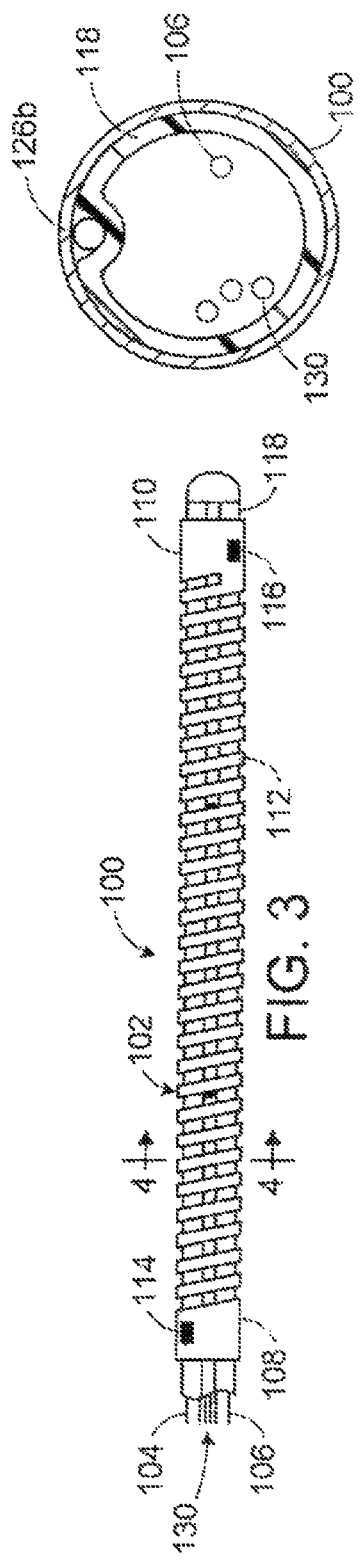

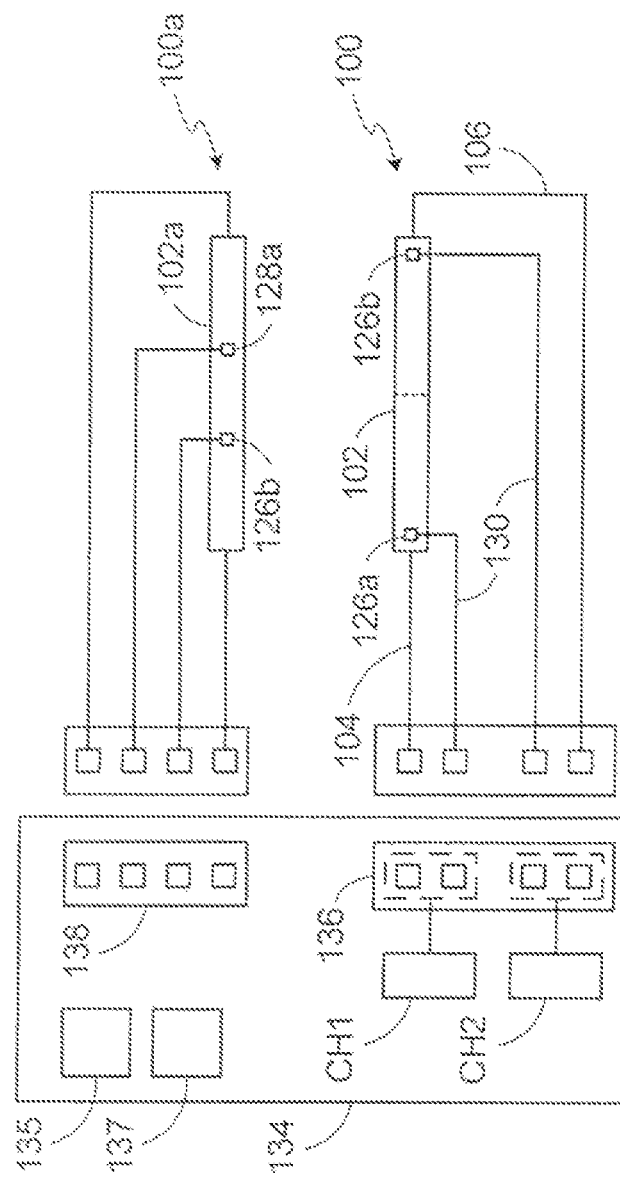

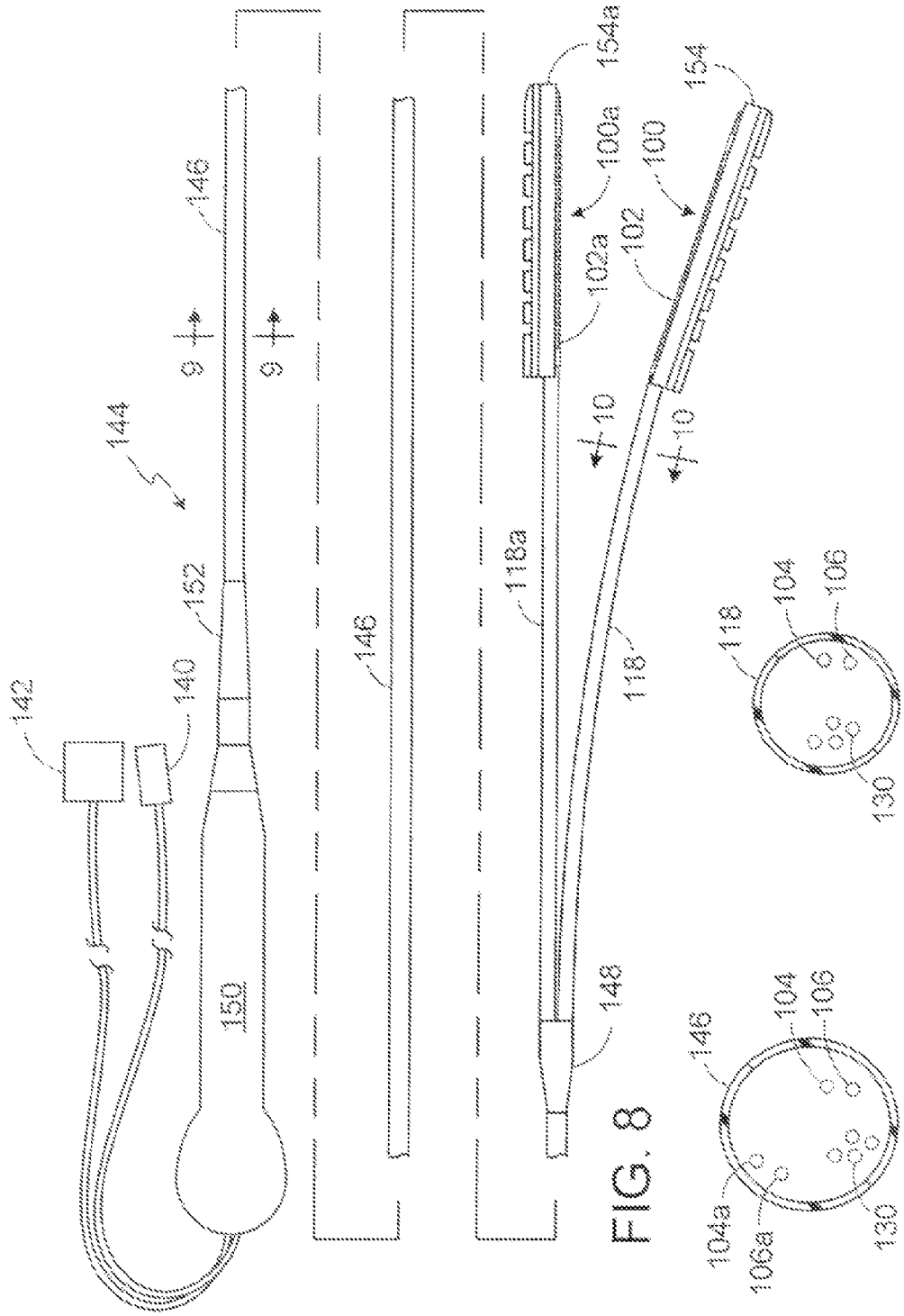

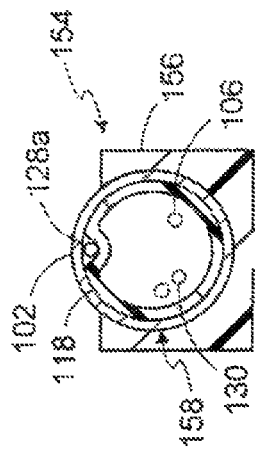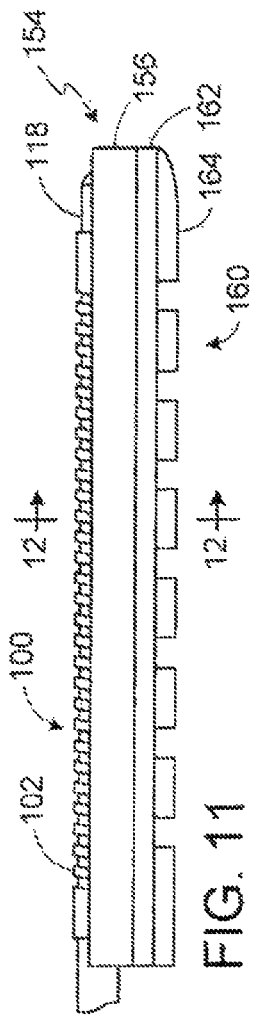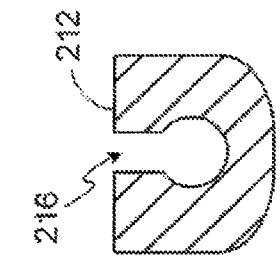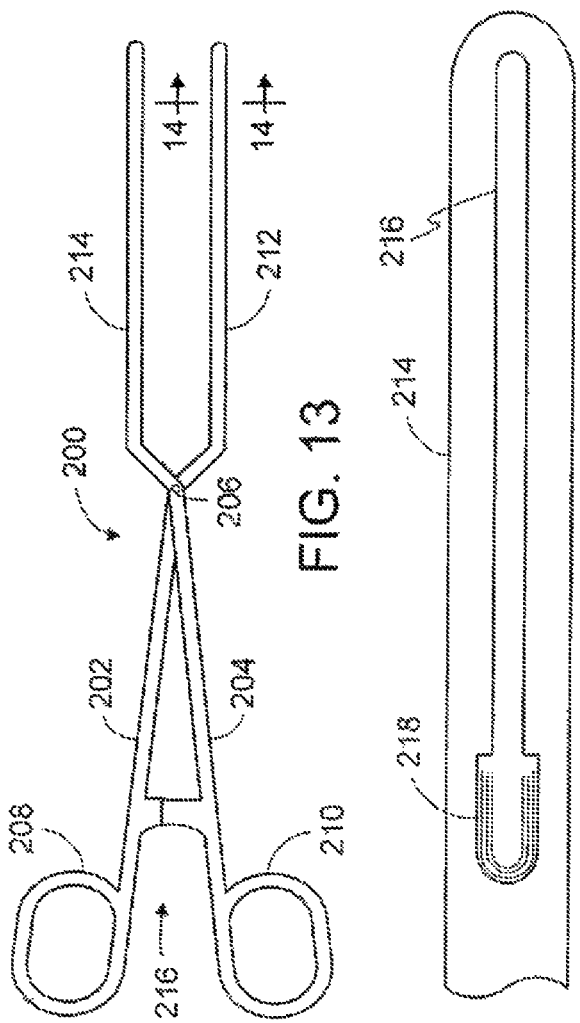

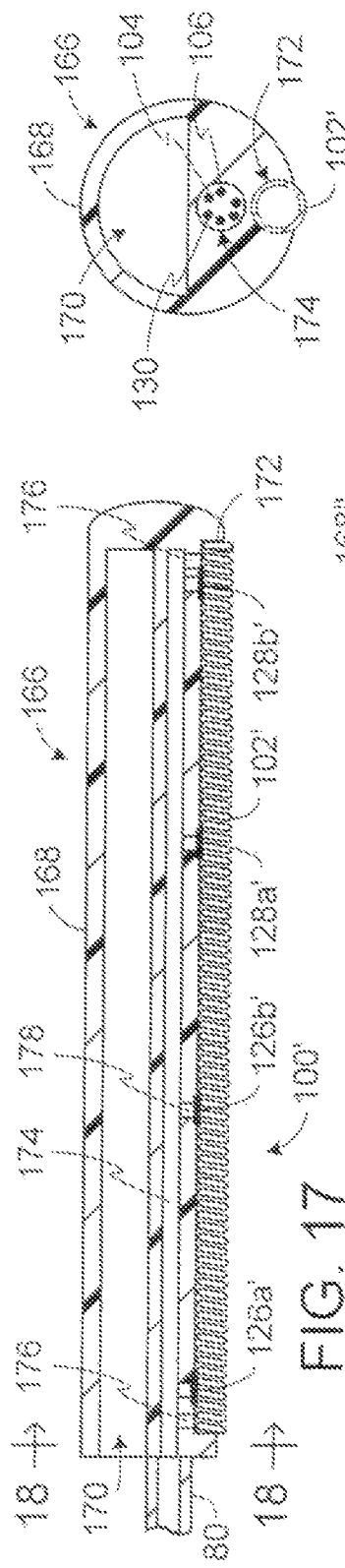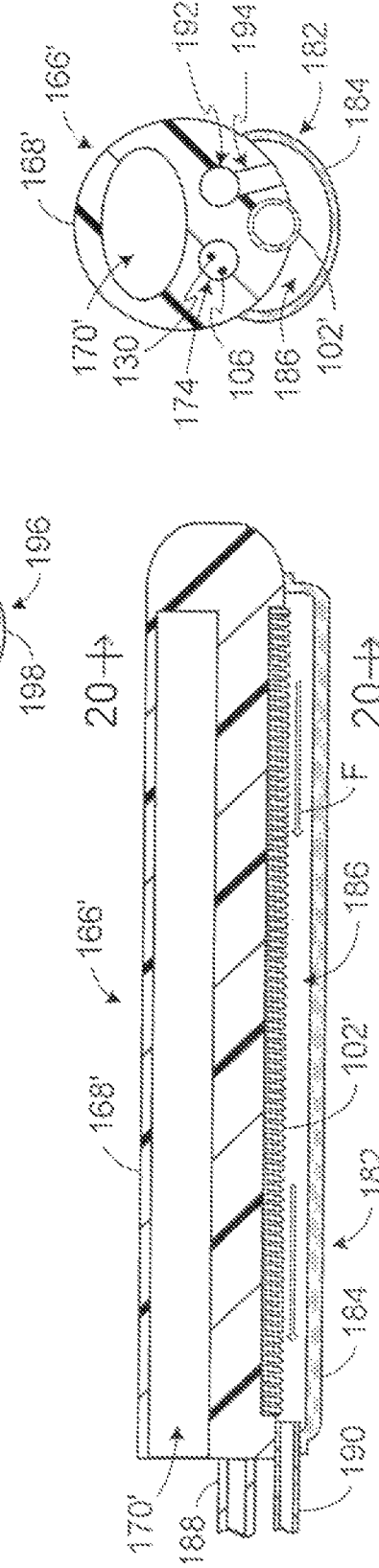

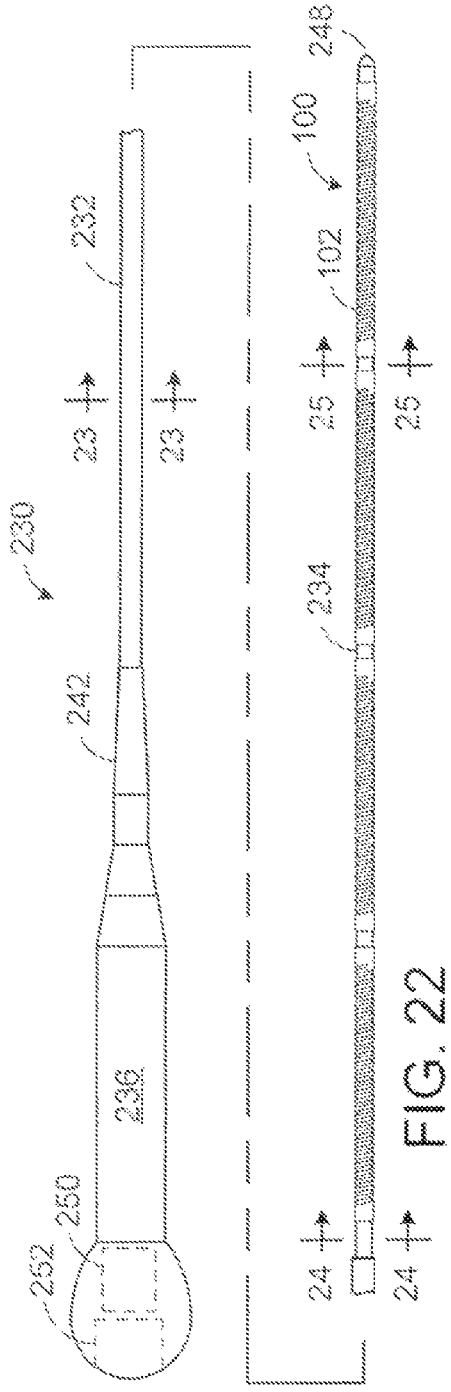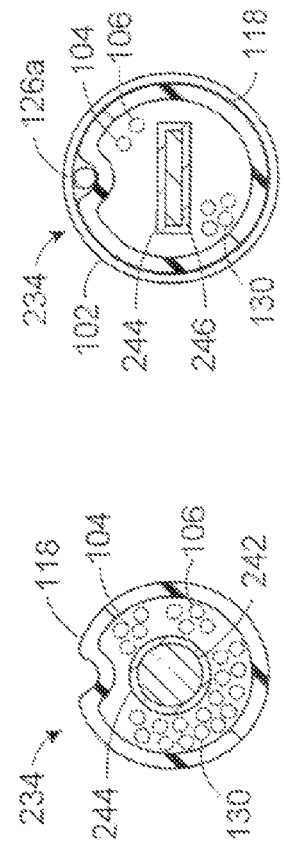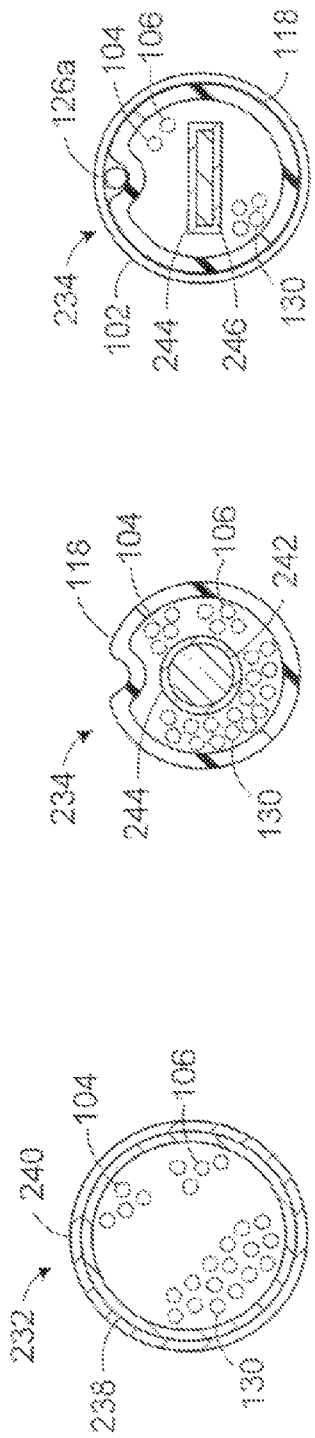

ELECTROPHYSIOLOGY ELECTRODE HAVING MULTIPLE POWER CONNECTIONS AND ELECTROPHYSIOLOGY DEVICES INCLUDING THE SAME

CROSS-REFERENCES TO RELATED APPLICATIONS

This application is a continuation of U.S. patent application Ser. No. 10/255,025, filed Sep. 24, 2002 (now U.S. Pat. No. 7,674,258), entitled "ELECTROPHYSIOLOGY ELECTRODE HAVING MULTIPLE POWER CONNECTIONS AND ELECTROPHYSIOLOGY DEVICES INCLUDING THE SAME," the entire disclosure of which is incorporated herein by reference.

STATEMENT AS TO RIGHTS TO INVENTIONS MADE UNDER FEDERALLY SPONSORED RESEARCH OR DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

BACKGROUND OF THE INVENTION

1. Field of Inventions

The present inventions relate generally to therapeutic elements and, more particularly, to therapeutic elements which are well suited for the formation of relatively long lesions in body tissue.

2. Description of the Related Art

There are many instances where therapeutic elements must be inserted into the body. One instance involves the formation of therapeutic lesions to the treat cardiac conditions such as atrial fibrillation, atrial flutter and arrhythmia. Therapeutic lesions may also be used to treat conditions in other regions of the body including, but not limited to, the prostate, liver, brain, gall bladder, uterus and other solid organs. Typically, the lesions are formed by ablating tissue with one or more electrodes. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soil tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue. Depending on the procedure, a variety of different electrophysiology devices may be used to position one or more electrodes at the target location. Each electrode is connected to a respective single power supply line and, in some instances, the power to the electrodes is controlled on an electrode-by-electrode basis. Examples of electrophysiology devices include catheters, surgical probes, and clamps.

Catheters used to create lesions typically include a relatively long and relatively flexible body that has one or more electrodes on its distal portion. The portion of the catheter body that is inserted into the patient is typically from 23 to 55 inches in length and there may be another 8 to 15 inches, including a handle, outside the patient. The proximal end of the catheter body is connected to the handle which includes steering controls. The length and flexibility of the catheter body allow the catheter to be inserted into a main vein or artery (typically the femoral artery), directed into the interior of the heart, and then manipulated such that the electrode contacts the tissue that is to be ablated. Fluoroscopic imaging is used to provide the physician with a visual indication of the location of the catheter. Exemplary catheters are disclosed in U.S. Pat. No. 5,582,609.

Surgical probes used to create lesions often include a handle, a relatively short shaft that is from 4 inches to 18 inches in length and either rigid or relatively stiff, and a distal section that is from 1 inch to 10 inches in length and either malleable or somewhat flexible. One or more electrodes are carried by the distal section. Surgical probes are used in epicardial and endocardial procedures, including open heart procedures and minimally invasive procedures where access to the heart is obtained via a thoracotomy, thoracostomy or median sternotomy. Exemplary surgical probes are disclosed in U.S. Pat. No. 6,142,994.

Clamps, which have a pair of opposable clamp members that may be used to hold a bodily structure or a portion thereof, are used in many types surgical procedures. Lesion creating electrodes have also been secured to certain types of clamps. Examples of clamps which carry lesion creating electrodes are disclosed in U.S. Pat. No. 6,142,994. Such clamps are particularly useful when the physician intends to position electrodes on opposite sides of a body structure in a bipolar arrangement.

The inventor herein has determined that, regardless of the type of electrophysiology device that is used, conventional apparatus and methods for forming therapeutic lesions are susceptible to improvement. For example, electrophysiology devices that are intended to form long lesions typically include a plurality of relatively short electrodes (typically about 10 mm). The inventor herein has determined that manufacturing costs could be reduced by reducing the number of electrodes without reducing the length of the lesions that the devices are capable of forming. The inventor herein has also determined that in some devices, such as bipolar clamps, the use of a plurality of spaced electrodes on opposite sides of a body structure may not be appropriate in all situations.

BRIEF SUMMARY OF THE INVENTION

An electrode assembly in accordance with the present inventions includes an electrode that is connected to at least two power supply lines. The present electrode assembly also provides a number of advantages over conventional electrode arrangements. For example, the present electrode assembly facilitates the formation of elongate lesions with fewer electrodes than conventional electrode arrangements.

The electrode assembly (or a plurality of electrode assemblies) may be used in electrophysiology devices including, but not limited to, catheters, surgical probes and clamps. In one exemplary bipolar clamp implementation, the present electrode assembly is provided on one clamp member and a similar electrode assembly (with an electrode and a pair of power return lines) is provided on the other clamp member. Such a clamp may be used to form long, continuous lesions without the gaps that may sometimes occur when a plurality of spaced power transmitting electrodes are positioned opposite a plurality of spaced return electrodes.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a plan view of an electrode assembly in accordance with a preferred embodiment of a present invention.

FIG. 2 is a plan view of an electrode support structure in accordance with a preferred embodiment of a present invention.

FIG. 3 is a plan view of an electrode assembly and electrode support structure in accordance with a preferred embodiment of a present invention.

FIG. 4 is a section view taken along line 4-4 in FIG. 3.

FIG. 6B is a diagrammatic view of a system in accordance with a preferred embodiment of a present invention.

FIG. 8 is a plan view of an energy transmission assembly in accordance with a preferred embodiment of a present invention.

FIG. 9 is a section view taken along line 9-9 in FIG. 8.

FIG. 10 is a section view taken along line 10-10 in FIG. 8.

FIG. 11 is an enlarged view of a portion of the energy transmission assembly illustrated in FIG. 8.

FIG. 12 is a section view taken along line 12-12 in FIG. 11.

FIG. 13 is a plan view of a clamp in accordance with a preferred embodiment of a present invention.

FIG. 14 is a section view taken along line 14-14 in FIG. 13.

FIG. 15 is a top view of a portion of the clamp illustrated in FIG. 13.

FIG. 17 is a section view of an energy transmission assembly in accordance with a preferred embodiment of a present invention.

FIG. 18 is a section view taken along line 18-18 in FIG. 17.

FIG. 19 is a section view of an energy transmission assembly in accordance with a preferred embodiment of a present invention.

FIG. 20 is a section view taken along line 20-20 in FIG. 19.

FIG. 21 is a section view of an energy transmission assembly in accordance with a preferred embodiment of a present invention.

FIG. 22 is a plan view of a surgical probe in accordance with a preferred embodiment of a present invention.

FIG. 23 is a section view taken along line 23-23 in FIG. 22.

FIG. 24 is a section view taken along line 24-24 in FIG. 22.

FIG. 25 is a section view taken along line 25-25 in FIG. 22.

DETAILED DESCRIPTION OF THE INVENTION

Figure 5:
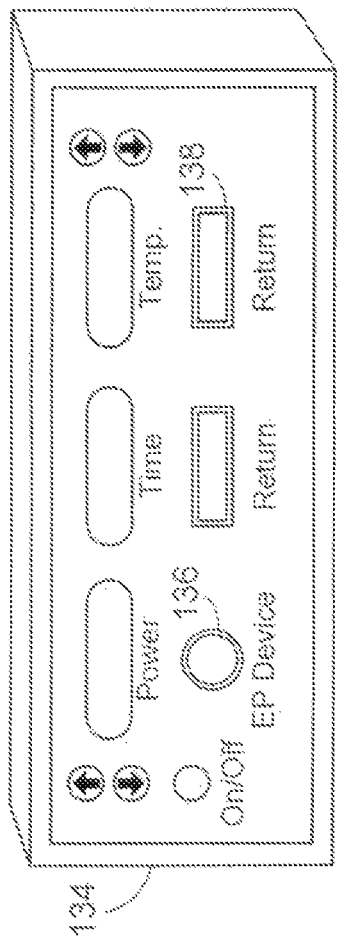
FIG. 5 is a front perspective view of a power supply and control device in accordance with a preferred embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
Electrodes, Temperature Sensing and Power Control
Energy Transmission Assemblies
Surgical Probes The section titles and overall organization of the present detailed description are for the purpose of convenience only and are not intended to limit the present inventions.

Electrodes, Temperature Sensing and Power Control

As illustrated for example in FIG. 1, an electrode assembly 100 in accordance with a preferred embodiment of a present invention includes an electrode 102 and first and second power supply lines 104 and 106 that are connected to the electrode. In other words, the electrode assembly 100 is configured such that power is supplied to the electrode 102 at least two locations. The power will preferably, although not necessarily, be supplied to each of the locations simultaneously. In the exemplary implementation, the electrode 102 includes first and second generally cylindrical base portions 108 and 110 and a helical portion 112. The power supply lines 104 and 106 are respectively connected to the base portions 108 and 110 by welds 114 and 116.

Although the present electrode is not limited to any particular electrode configuration, the exemplary electrode 102 is preferably a spiral (or "helical") coil that is relatively flexible. The exemplary electrode 102 is made of electrically conducting material, like copper alloy, platinum, or stainless steel, or compositions such as drawn-filled tubing (e.g. a copper core with a platinum jacket). The electrically conducting material can be further coated with platinum iridium or gold to improve its conduction properties and biocompatibility. An exemplary coil electrode configuration is disclosed in U.S. Pat. No. 5,797,905. With respect to the manufacture of a helical electrode, such an electrode may be manufactured by, for example, laser cutting a hypotube (FIG. 1) or winding wire that is either round or rectangular in cross-section into the desired shape (FIG. 17).

The structural and electrical characteristics of the electrode 102, which will vary from application to application, are preferably such that the power supplied to one portion of the electrode will be substantially dissipated before it reaches a portion of the electrode to which power is being independently supplied. For cardiovascular applications, the length is preferably between about 2 cm and 8 cm in those instances where power is supplied at the longitudinal ends and the end to end resistance is about 5 ohm to about 15 ohm. Typically, about 80% of the power supplied to one of the ends will be dissipated prior to reaching the mid-point of the electrode. Such a combination of characteristic facilitates regional power control of the electrode in the manner described below with reference with FIGS. 5-7. The diameter preferably ranges from about 1.5 mm to about 3 mm for cardiovascular applications. In one preferred implementation where a laser cut hypotube is connected to a source of RF energy at each of its longitudinal ends, the wall thickness of the hypotube is about 0.12 mm, the length is 6.4 cm, the outer diameter is about 2 mm, and the end to end resistance is about 10 ohms.

In an exemplary three power supply line embodiment that is otherwise essentially identical to the two power supply line embodiment described above, the electrode preferably includes a third base portion at the mid-point between the base portions at the longitudinal ends of the electrode. The three power supply lines are respectively connected to the three base portions. Here, the length of the electrode preferably ranges from about 6 cm to about 12 cm and the resistance between adjacent base portions will be about 5 ohm to about 15 ohm and, in a preferred implementation, about 10 ohms.

As an alternative, the electrodes may be in the form of solid rings of conductive material, like platinum, or can comprise a conductive material, like platinum-iridium or gold, coated upon an underlying non-conductive support member using conventional coating techniques or an ion beam assisted deposition (IBAD) process. For better adherence, an undercoating of nickel or titanium can be applied. The electrodes can also be formed with a conductive ink compound that is pad printed onto an underlying non-conductive support member. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Power may also be supplied to these alternative electrodes at two or more positions.

Turning to FIGS. 2-4, the electrode 102 may be carried by a support structure 118. The exemplary support structure 118 is a flexible tubular structure which has an outer diameter that is, depending on the diameter of the electrode 102, typically between about 1.5 mm and about 3 mm. The support structure 118 in the illustrated embodiment, which is intended for use in cardiovascular applications, has an outer diameter of about 2 mm. Suitable support structure materials include, for example, flexible biocompatible thermoplastic tubing such as upbraided Pebax® material, polyethylene, or polyurethane tubing. The support structure 118 is provided with a pair of apertures 120 and 122 for the power supply lines 104 and 106 as well as a tip member 124.

A plurality of temperature sensors, such as thermocouples or thermistors, may be located on or under the electrode 102 for temperature control purposes. In the exemplary implementation, two pairs of temperature sensors 126a/126b and 128a/128b are employed. Each of the temperature sensors operate independently of one another. Temperature sensors 126a and 128b are located at the longitudinal edges of the electrode 102, while temperature sensors 126b and 128a are spaced a distance equal to about ⅓ of the total electrode length from the respective longitudinal ends of the electrode. A third pair of temperature sensors could be provided in the aforementioned embodiment in which three power supply lines are connected to the electrode. In some embodiments, a reference thermocouple (not shown) may also be provided on the support structure 118 in spaced relation to the electrode 102. Signals from the temperature sensors are transmitted to a power supply and control device by way of signal lines 130.

The temperature sensors 126a/126b and 128a/128b are preferably located within a linear channel 132 that is formed in the support structure 118. The linear channel may extend over the entire length of the support structure 118 or only over the portion that carries the electrode (or electrodes) 102. The linear channel 132 insures that the temperature sensors will all face in the same direction (e.g. facing tissue) and be arranged in linear fashion. This arrangement results in more accurate temperature readings which, in turn, results in better temperature control. As such, the actual tissue temperature will more accurately correspond to the temperature set by the physician on the power supply and control device, thereby providing the physician with better control of the lesion creation process and reducing the likelihood that embolic materials will be formed. Such a channel may be employed in conjunction with any of the electrode support structures disclosed herein.

Figure 6A:
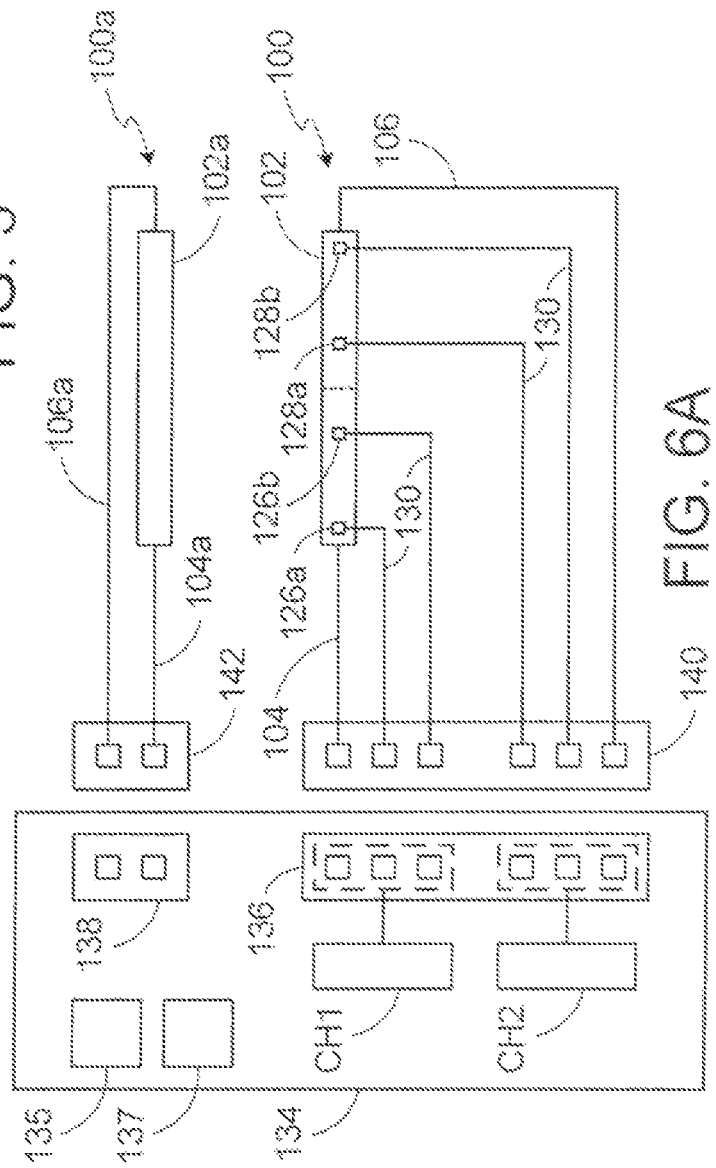
FIG. 6A is a diagrammatic view of a system in accordance with a preferred embodiment of a present invention.

As illustrated for example in FIGS. 5 and 6A, the electrode assembly 100 may be used in conjunction with an electrosurgical unit ("ESU") 134 that supplies and controls power, such RF power. A suitable ESU is the Model 4810 ESU sold by Boston Scientific Corporation of Natick, Mass. The exemplary ESU 134 illustrated in FIG. 5 includes a controller 135, a source of RF power 137 that is controlled by the controller, and a plurality of displays and buttons that are used to set the level of power supplied to the electrode 102 and the temperature at various locations on the electrode. The exemplary ESU 134 illustrated is operable in a bipolar mode, where tissue coagulation energy emitted by the electrode 102 is returned through a return electrode 102a, and a unipolar mode, where the tissue coagulation energy emitted by the electrode is returned through one or more indifferent electrodes (not shown) that are externally attached to the skin of the patient with a patch or one or more electrodes (not shown) that are positioned in the blood pool. The return electrode 102x, which in a bipolar configuration is preferably (but not necessarily) identical to the electrode 102, may be connected to the ESU 134 by a pair of power return lines 104a and 106a. The return electrode 102a and power return lines 104a and 106a together define a return electrode assembly 100a.

The ESU 134 in the illustrated implementation is provided with a power output connector 136 and a pair of return connectors 138. The electrode 102 is connected to the power output connector 136 by way of the power supply lines 104 and 106 and a power connector 140, while the return electrode 102a is connected to one of the return connectors 138 by way of the power return lines 104a and 106a and a return connector 142. In a preferred implementation, the ESU output and return connectors 136 and 138 have different shapes to avoid confusion and the power and return connectors 140 and 142 are correspondingly shaped. In the exemplary bipolar energy transmission assembly 144 illustrated in FIG. 8, for example, the power connector 140 has a generally circular shape corresponding to the ESU power output connector 136 and the return connector 142 has a generally rectangular shape corresponding to the ESU return connector 138. Signals from the temperature sensors 126a/126b and 128a/128b are transmitted to the ESU 134 by way of the signal lines 130 and the power connector 140.

Figure 7:
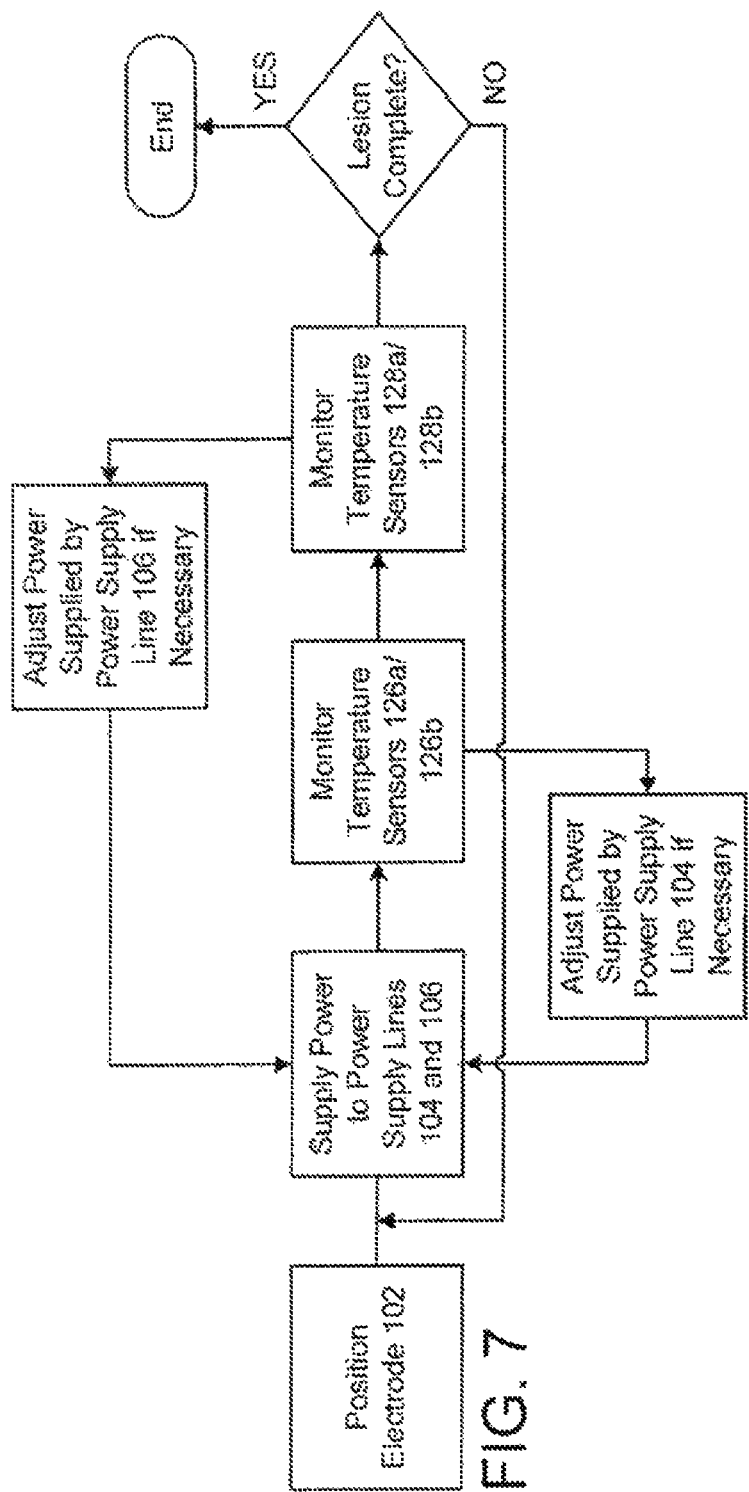
FIG. 7 is a flow chart of a method in accordance with a preferred embodiment of the present invention.

The exemplary ESU 134 illustrated in FIGS. 5 and 6A is configured to individually power and control a plurality of electrodes (typically relatively short electrodes that are about 10 mm in length). This is sometimes referred to as "multi-channel control" and the ESU 134 preferably includes up to 8 channels. The exemplary ESU 134 is also configured to individually power and control two or more portions of a single electrode as well as two or more portions of each of a plurality of electrodes during a lesion formation procedure. The electrode 102 in the exemplary implementation is divided into two portions for power control purposes—the electrode portion connected to the power supply line 104 on one side of the dash line in FIG. 6A and the electrode portion connected to the power supply line 106 on the other side of the dash line. [It should be emphasized that this is not a physical division and that the electrode 102 is preferably a continuous, unitary structure]. The electrode 102 is placed adjacent to tissue and power to one portion is controlled by control channel CH1 and power to the other portion is controlled by control channel CH2. The power is preferably, although not necessarily, supplied to both portions simultaneously. The above-described power supply/lesion formation method is illustrated in FIG. 7.

More specifically, the level of power supplied to the electrode 102 by way of the power supply line 104 may be controlled based on the temperatures sensed by the temperature sensors 126a/126h, while the level of power supplied to the electrode 102 by way of the power supply line 106 may be controlled based on the temperatures sensed by the temperature sensors 128a/128b. In one exemplary control scheme, the level of power supplied to the electrode 102 by way of the power supply line 104 would be controlled based on the highest of the two temperatures sensed by the temperature sensors 126a/126b, while the level of power supplied to the electrode 102 by way of the power supply line 106 would be controlled based on the highest of the two temperatures sensed by the temperature sensors 128a/128b.

The amount of power required to coagulate tissue typically ranges from 5 to 150 w. Suitable temperature sensors and power control schemes that are based on sensed temperatures are disclosed in U.S. Pat. Nos. 5,456.682, 5,582,609 and 5,755,715.

The actual number and location of the temperature sensors may be varied in order to suit particular applications. As illustrated for example in FIG. 6B, the temperature sensors 126b and 128a may be located on the return electrode 102a in certain bipolar implementations, such as the exemplary bipolar energy transmission assembly 144 illustrated in FIG. 8. Nevertheless, the power control scheme will preferably be the same in that the level of power supplied to the electrode 102 by way of the power supply line 104 would be controlled based on the temperatures sensed by the temperature sensors 126a/126b, while the level of power supplied to the electrode 102 by way of the power supply line 106 would be controlled based on the temperatures sensed the temperature sensors 128a/128b.

In those instances where a plurality of spaced electrodes 102 are provided, such as in the surgical probe 230 illustrated in FIG. 22 that operates in a unipolar mode, each of the electrodes will preferably be connected to a respective pair of power supply lines 104 and 106 and include its own set of temperature sensors 126a/126b and 128a/128b. Each of the electrodes 102 on the surgical probe 230 will also preferably be divided into two portions for power control purposes and the level of power supplied to the each electrode portion by way of the power supply lines 104 would be controlled based on the temperatures sensed by the temperature sensors 126a/126b, while the level of power supplied to the electrode portions by way of the power supply lines 106 would be controlled based on the temperatures sensed by the temperature sensors 128a/128b.

Energy Transmission Assemblies

The electrodes 102 may be used conjunction with a wide variety of electro physiology devices. One example is an energy transmission assembly, which is an electrophysiology device that may be combined with a conventional surgical tool to form a tissue coagulating device. Although the present invention are not limited to any particular surgical tool, clamps are one example of a surgical tool that may be used in conjunction with energy transmission assemblies in accordance with the present inventions. As used herein, the term "clamp" includes, but is not limited to, clamps, clips, forceps, hemostats, and any other surgical device that includes a pair of opposable clamp members that hold tissue, at least one of which is movable relative to the other in some instances, the clamp members are connected to a scissors-like arrangement including a pair of handle supporting arms that are pivotably connected to one another. The clamp members are secured to one end of the arms and the handles are secured to the other end. Certain clamps that are particularly useful in minimally invasive procedures also include a pair of handles and a pair of clamp members. Here, however, the clamp members and handles are not mounted on the opposite ends of the same arm. Instead, the handles are carried by one end of an elongate housing and the clamp members are carried by the other. A suitable mechanical linkage located within the housing causes the clamp members to move relative to one another in response to movement of the handles. The clamp members may be linear or have a predefined curvature that is optimized for a particular surgical procedure or portion thereof. The clamp members may also be rigid or malleable.

Figure 16:
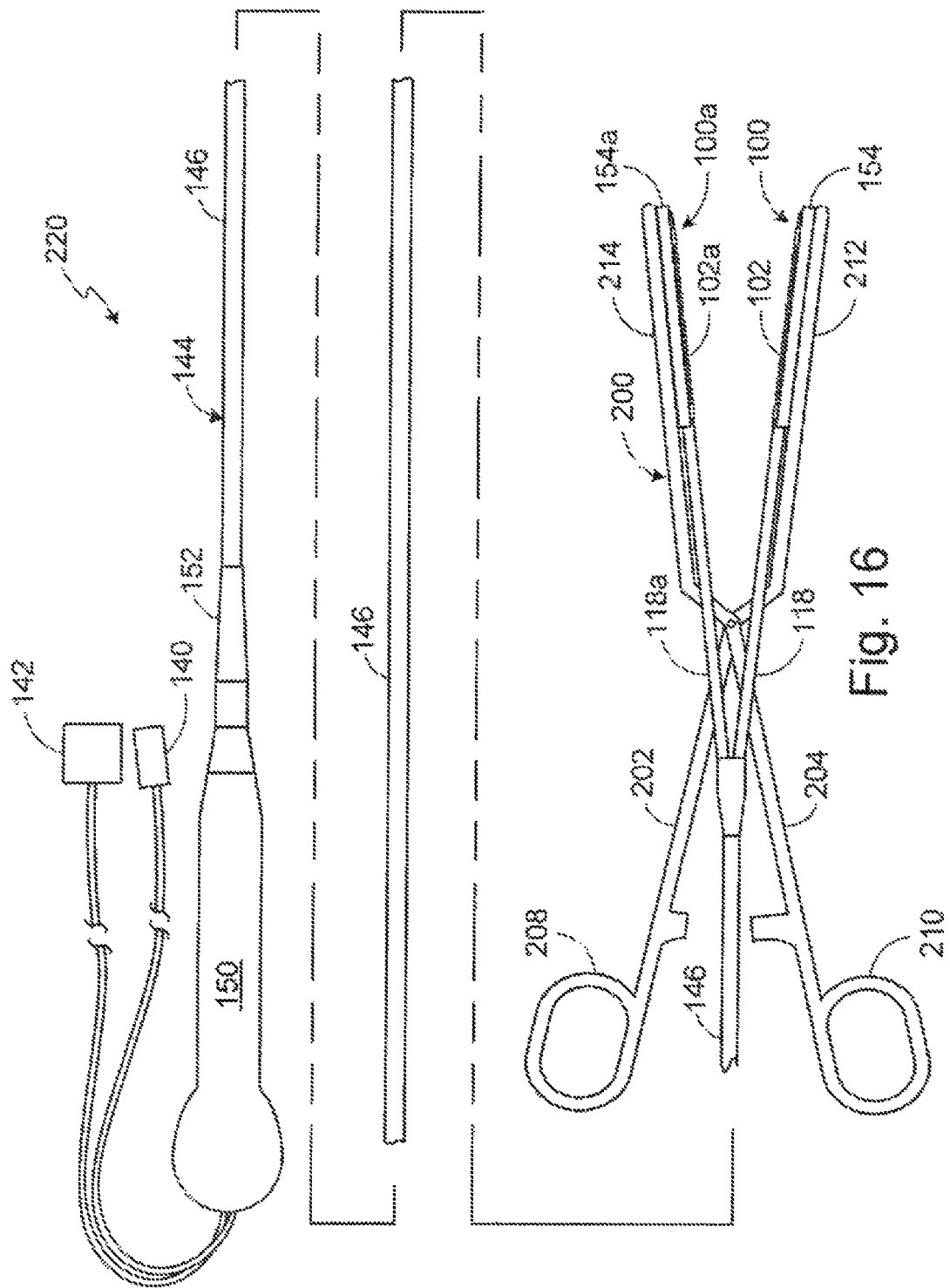
FIG. 16 is a plan view showing the energy transmission assembly illustrated in FIG. 8 in combination with the clamp illustrated in FIG. 13.

In one implementation, the exemplary energy transmission assembly that is generally represented by reference numeral 144 in FIGS. 8-12 may be used to covert the conventional clamp 200 illustrated in FIGS. 13-15 into the tissue coagulation device 220 illustrated in FIG. 16. Referring first to FIGS. 13-15, one example of a conventional clamp that may be used in conjunction with the present inventions is generally represented by reference numeral 200. The clamp 200 includes a pair of rigid arms 202 and 204 that are pivotably connected to one another by a pin 206. The proximal ends of the arms 202 and 204 are respectively connected to a pair handle members 208 and 210, while the distal ends are respectively connected to a pair of clamp members 212 and 214. The clamp members 212 and 214 may be rigid or malleable and, if rigid, may be linear or have a pre-shaped curvature. A locking device 216 locks the clamp in the closed orientation, and prevents the clamp members 212 and 214 from coming any closer to one another than is illustrated in FIG. 13, thereby defining a predetermined spacing between the clamp members. The clamp 200 is also configured for used with a pair of soft, deformable inserts (not shown) that may be removably carried by the clamp members 212 and 214 and allow the clamp to firmly grip a bodily structure without damaging the structure. To that end, the clamp members 212 and 214 are each include a slot 216 that is provided with a sloped inlet area 218 and the inserts include mating structures that are removably friction fit within the slots. The present energy transmission assemblies may be mounted on the clamp members in place of the inserts.

Turning to FIGS. 8-10, the exemplary energy transmission assembly 144 includes a power transmitting electrode assembly 100 (i.e. an electrode 102 and first and second power supply lines 104 and 106) and a return electrode assembly 100a (i.e. an electrode 102a and first and second power supply lines 104a and 106a). The electrode assemblies 100 and 100a are carried on respective support structures 118 and 118a. The support structures 118 and 118a are connected to a flexible cable 146 by a molded plastic junction 148. The first and second power supply lines 104 and 106 and signal lines 130 run from the electrode 102 extend through the support structure 118 and the cable 146 to the connector 140. The first and second power return lines 104a and 106a run from the electrode 102x, through the support structure 118a and the cable 146 to the connector 142. In the exemplary implementation, the cable 146 is secured to a handle 150 with a strain relief element 152.

The exemplary energy transmission assembly 144 also includes a pair of base members 154 and 154a which are used to connect the electrode assemblies 100 and 100a to the clamp 200. Although the configuration of the energy transmission assemblies 144 may vary from application to application to suit particular situations, the exemplary energy transmission assembly is configured such that the electrodes 102 and 102a will be parallel to one another as well as relatively close to one another (i.e. a spacing of about 1-10 mm) when the clamp 200 is in the closed orientation. Such an arrangement will allow the energy transmission assembly to grip a bodily structure without cutting through the structure. Referring more specifically to FIGS. 11-15, the base member 154 includes a main portion 156, with a groove 158 that is configured to receive the support structure 118 and electrode 102, and a connector 160 that is configured to removably mate with the slot 216 in the clamp 200. [It should be noted that the configuration of the base member 154a is identical to that of the base member 154 in the illustrated embodiment.] About 20% of the electrode surface (i.e. about 75° of the 360° circumference) is exposed in the illustrated embodiment. Adhesive may be used to hold the support structure 118 and electrode 102 in place. The exemplary connector 160 is provided with a relatively thin portion 162 and a relatively wide portion 164, which may consist of a plurality of spaced members (as shown) or an elongate unitary structure, in order to correspond to the shape of the slot 216.

The base members 154 and 154a are preferably formed from polyurethane. The length oldie base members in the exemplary energy transmission assemblies will vary according to the intended application. In the area of cardiovascular treatments, it is anticipated that suitable lengths will range from, but are not limited to, about 4 cm to about 10 cm. In the exemplary implementation, where the electrodes 102 and 102a are preferably about 6.4 cm, the base members 154 and 154a will be about 6.6 cm.

As illustrated for example in FIG. 16, the exemplary energy transmission assembly 144 and clamp 200 may be combined to form a tissue coagulation device 220. More specifically, the electrode assemblies 100 and 100a may be secured to the clamp members 212 and 214 by the base members 154 and 154a. The coagulation device 220 may be used to form a lesion by, for example, positioning the electrode assemblies 100 and 100a on opposite sides of a tissue structure with the clamp members 212 and 214. Energy from a power supply and control device (such as the ESU 134 illustrated in FIG. 5) may be transmitted to both longitudinal ends of the electrode 102 by way of the connector 140 and returned to the power supply and control device by way of the electrode 102a and connector 142.

One example of a procedure that may be performed with the exemplary tissue coagulation device 220 is the formation of transmural epicardial lesions to isolate the sources of focal (or ectopic) atrial fibrillation and, more specifically, the creation of transmural lesions around the pulmonary veins. Lesions may be created around the pulmonary veins individually or, alternatively, lesions may be created around pairs of pulmonary veins. For example, a first transmural epicardial lesion may be created around the right pulmonary vein pair and a second transmural epicardial lesion may be created around the left pulmonary vein pair. Thereafter, if needed, a linear transmural epicardial lesion may be created between the right and left pulmonary vein pairs. A linear transmural lesion that extends from the lesion between the right and left pulmonary vein pairs to the left atrial appendage may also be formed. These linear lesions may be formed with the tissue coagulation device 220 by forming a hole in the atria, inserting one of the clamp members (and corresponding electrode assembly) into the atria, and then closing the clamp members along the desired portion of the atria. Alternatively, a linear transmural epicardial lesion may be formed with the surgical probe illustrated in FIG. 22. It should also be noted that, instead of forming multiple lesions, a single lesion may be formed around all four of the pulmonary veins.

The exemplary energy transmission assembly 144 may be modified in a variety of ways. For example, a layer of Dacron or a Dacron/collagen composite may be placed over the exposed surface of the electrodes 102 and 102x. This material, when wetted with saline, reduces tissue desiccation and makes current densities more uniform. As such, surface char is avoided and transmural lesion formation is ensured.

The base members that carry the electrode assemblies may also be reconfigured in order to account for situations where the associated clamp lacks the aforementioned slots 216. As illustrated for example in FIGS. 17 and 18, the energy transmitting portion of an exemplary energy transmission assembly 166 includes an electrode assembly 100' and a base member 168 that carries an electrode 102' (thereby acting as a support structure) and is configured to be removably slipped over and secured to a clamp member, such as one of the clamp members 212 and 214. The electrode assembly 100' is substantially similar to the electrode assembly 100. Here, however, the electrode 102' is in the form of a wound wire (although a laser cut hypotube-type electrode could also be employed here). In one exemplary implementation, the energy transmission assembly will be a bipolar arrangement that includes a second generally identical base member and electrode, as is discussed above with reference to FIG. 8. Such a bipolar energy transmission assembly may be configured such that the transmitting and return electrodes will be parallel to one another as well as relatively close to one another when the clamp is in the closed orientation in order to allow the energy transmission assembly to grip a bodily structure without cutting through the structure. Alternatively, in a unipolar implementation, the structure illustrated in FIGS. 17 and 18 may be used in combination with an indifferent electrode that is externally attached to the skin of the patient with a patch or one or more electrodes that are positioned in the blood pool.

The exemplary base member 168 is preferably formed from a soft, resilient, low durometer material that is electrically insulating. Suitable materials include polyurethane, silicone and polyurethane/silicone blends having a hardness of between about 20 Shore D and about 72 Shore D. The base member 168 includes a longitudinally extending aperture 170 into which the clamp member may be inserted. The aperture 170 should be sized and shaped such that the base member 168 will be forced to stretch when the clamp member is inserted. If, for example, the aperture 170 has the same cross-sectional shape as the clamp member (e.g. both are elliptical), then the aperture should be slightly smaller in their cross-sectional dimensions than the corresponding clamp member. The stretching of the apertures 170 creates a tight interference fit between the base member 168 and clamp member. Additionally, although the aperture 170 has a semi-circular cross-section in the exemplary embodiment, the aperture may have a round, rectangular, square or elliptical cross-section, or define any other cross-sectional shape, depending on the particular application.

The exemplary base member 168 also includes a slot 172 that secures the electrode assembly 100' in place. The configuration of the slot 172 will, of course, depend on the configuration of the electrode assembly that it is holding. The illustrated electrode 102' is generally cylindrical in shape and the slot 172 has a corresponding arcuate cross-sectional shape. The arc is preferably greater than 180 degrees so that the base member 168 will deflect when the electrode 102' is inserted into the slot 172 and then snap back to hold the electrode in place. Adhesive may also be used to secure the electrode 102', especially in those instances where the arc is less than 180 degrees.

In order to accommodate the power supply lines 104 and 106 and the temperature sensor signal lines 130 (FIG. 18), the exemplary base member 168 is also provided with a wire aperture 174, a pair of power line holes 176 and four signal line holes 178 for the temperature sensors 126a'/126b' and 128a'/128b'. The number of power line and signal line holes will, of course, depend on the configuration of the electrode assembly 100'. A cable 180 provided for the power supply lines 104 and 106 and temperature sensor signal lines 130.

Energy transmission assemblies in accordance with the present inventions may also be provided with apparatus that cools the tissue during tissue coagulation procedures. The tissue cooling apparatus disclosed herein employ conductive fluid to cool tissue during coagulation procedures. More specifically, and as described below and in U.S. application Ser. No. 09/761,981, which is entitled "Fluid Cooled Apparatus For Supporting Diagnostic And Therapeutic Elements In Contact With Tissue" and incorporated herein by reference, heat from the tissue being coagulated is transferred to ionic fluid to cool the tissue while energy is transferred from an electrode or other energy transmission device to the tissue through, the fluid by way of ionic transport. The conductive fluid may be pumped through the tissue cooling apparatus (FIGS. 19 and 20) or the tissue cooling apparatus may be saturated with the fluid prior to use (FIG. 21). In either case, cooling tissue during a coagulation procedure facilitates the formation of lesions that are wider and deeper than those that could be realized with an otherwise identical device which lacks tissue cooling apparatus. Preferably, tissue cooling apparatus will be associated with both the transmitting electrode and the return electrode in a bipolar implementation.

Referring first to FIGS. 19 and 20, the energy transmitting portion of an exemplary energy transmission assembly 166' includes an electrode 102' and a base member 168' that carries the electrode and is configured to be removably secured to a clamp member, such as one of the clamp members 212 and 214. Many aspects of the exemplary energy transmission assembly 166' are substantially similar to the assembly 166 and similar elements are represented by similar reference numerals. Here, however, a tissue cooling apparatus 182 is also provided. In one exemplary implementation, the energy transmission assembly will be a bipolar arrangement that includes a second generally identical base member, electrode and cooling apparatus, as is discussed above with reference to FIG. 8. Such a bipolar energy transmission assembly may be configured such that the transmitting and return electrodes will be parallel to one another as well as relatively close to one another when the clamp is in the closed orientation in order to allow the energy transmission assembly to grip a bodily structure without cutting through the structure. Alternatively, in a unipolar implementation, the structure illustrated in FIGS. 19 and 20 may be used in combination with an indifferent electrode that is externally attached to the skin of the patient with a patch or one or more electrodes that are positioned in the blood pool. Additionally, although the aperture 170' has an elliptical cross-section in the exemplary embodiment, the apertures may have a round, rectangular, square or semi-circular cross-section, or define any other cross-sectional shape, depending on the particular application.

The exemplary tissue cooling apparatus 182 includes a nanoporous outer casing 184 through which ionic fluid (represented by arrows F) is transferred. The ionic fluid preferably flows from one longitudinal end of the tissue cooling apparatus 182 to the other. The outer casing 184 is secured to the base member 168' over the electrode 102' such that a fluid transmission space 186 is defined therebetween. More specifically, the proximal and distal ends of the outer casing 184 are secured to the base member 168' with anchoring devices (not shown) such as lengths of heat shrink tubing, Nitinol tubing or other mechanical devices that form an interference fit between the casing and the base member. Adhesive bonding is another method of securing the outer casing 184 to the base member 168'. The fluid transmission space will typically be about 0.5 mm to about 2.0 mm high and slightly wider than the associated electrode 102'.

The ionic fluid is supplied under pressure from a fluid source (not shown) by way of a supply line 188 and is returned to the source by way of a return line 190 in the exemplary implementation illustrated in FIGS. 19 and 20. The supply line 188 is connected to a fluid lumen 192 that runs from the proximal end of the base member 168' to the distal region of the outer casing 184. The fluid lumen 192 is connected to the fluid transmission space 186 by an aperture 194.

The electrically conductive ionic fluid preferably possesses a low resistivity to decrease ohmic loses, and thus ohmic heating effects, within the outer casing 184. The composition of the electrically conductive fluid can vary. In the illustrated embodiment, the fluid is a hypertonic saline solution, having a sodium chloride concentration at or near saturation, which is about 5% to about 25% weight by volume. Hypertonic saline solution has a relatively low resistivity of only about 5 ohm-cm, as compared to blood resistivity of about 150 ohm-cm and myocardial tissue resistivity of about 500 ohm-cm. Alternatively, the ionic fluid can be a hypertonic potassium chloride solution.

With respect to temperature and flow rate, a suitable inlet temperature for epicardial applications (the temperature will, of course, rise as heat is transferred to the fluid) is about 0 to 25° C. with a constant flow rate of about 2 to 20 ml/min. The flow rate required for endocardial applications where blood is present would be about three-fold higher (i.e. 6 to 60 ml/min.). Should applications so require, a flow rate of up to 100 ml/min. may be employed. In a closed system where the fluid is stored in a flexible bag, such as the Viaflex® bag manufactured by Baxter Corporation, and heated fluid is returned to the bag, it has been found that a volume of fluid between about 200 and 500 ml within the bag will remain at room temperature (about 22° C.) when the flow rate is between about 2 ml/min. and 20 ml/min. Alternatively, in an open system, the flexible bag should include enough fluid to complete the procedure. 160 ml would, for example, be required for a 20 minute procedure where the flow rate was 8 ml/min.

The fluid pressure within the outer casing 184 should be about 30 mm Hg in order to provide a structure that will resiliently conform to the tissue surface in response to a relatively small force normal to the tissue. Pressures above about 100 mm Hg will cause the outer casing 184 to become too stiff to properly conform to the tissue surface. For that reason, the flow resistance to and from the outer casing 184 should be relatively low.

The pores in the nanoporous outer casing 184 allow the transport of ions contained in the fluid through the casing and into contact with tissue. Thus, when the electrode 102' transmits RF energy into the ionic fluid, the ionic fluid establishes an electrically conductive path through the outer casing 184 to the tissue being coagulated. Regenerated cellulose membrane materials, typically used for blood oxygenation, dialysis or ultrafiltration, are a suitable nanoporous material for the outer casing 184. The thickness of the material should be about 0.002 to 0.005 inch. Although regenerated cellulose is electrically non-conductive, the relatively small pores of this material allow effective ionic transport in response to the applied RF field. At the same time, the relatively small pores prevent transfer of macromolecules through the material, so that pressure driven liquid perfusion is less likely to accompany the ionic transport, unless relatively high pressure conditions develop within the outer casing 184.

Hydro-Fluoro™ material, which is disclosed in U.S. Pat. No. 6,395,325, is another material that may be used. Materials such as nylons (with a softening temperature above 100° C.), PTFE, PEI and PEEK that have nanopores created through the use of lasers, electrostatic discharge, ion beam bombardment or other processes may also be used. Such materials would preferably include a hydrophilic coating. Nanoporous materials may also be fabricated by weaving a material (such as nylon, polyester, polyethylene, polypropylene, fluorocarbon, fine diameter stainless steel, or other fiber) into a mesh having the desired pore size and porosity. These materials permit effective passage of ions in response to the applied RF field. However, as many of these materials possess larger pore diameters, pressure driven liquid perfusion, and the attendant transport of macromolecules through the pores, are also more likely to occur.

The electrical resistivity of the outer casing 184 will have a significant influence on lesion geometry and controllability. Low-resistivity (below about 500 ohm-cm) requires more RF power and results in deeper lesions, while high-resistivity (at or above about 500 ohm-cm) generates more uniform heating and improves controllability. Because of the additional heat generated by the increased body resistivity, less RF power is required to reach similar tissue temperatures after the same interval of time. Consequently, lesions generated with high-resistivity structures usually have smaller depth. The electrical resistivity of the outer casing can be controlled by specifying the pore size of the material, the porosity of the material, and the water adsorption characteristics (hydrophilic versus hydrophobic) of the material. A detailed discussion of these characteristics is found in U.S. Pat. No. 5,961,513. A suitable electrical resistivity for epicardial and endocardial lesion formation is about 1 to 3000 ohm-cm measured wet.

Generally speaking, low or essentially no liquid perfusion through the nanoporous outer casing 184 is preferred. When undisturbed by attendant liquid perfusion, ionic transport creates a continuous virtual electrode at the tissue interface. The virtual electrode efficiently transfers RF energy without need for an electrically conductive metal surface. Pore diameters smaller than about 0.1 µm retain macromolecules, but allow ionic transfer through the pores in response to the applied RF field. With smaller pore diameters, pressure driven liquid perfusion through the pores is less likely to accompany the ionic transport, unless relatively high pressure conditions develop within the outer casing 184 Larger pore diameters (up to 8 µm) can also be used to permit ionic current flow across the membrane in response to the applied RF field. With larger pore diameters, pressure driven fluid transport across the membrane is much higher and macromolecules (such as protein) and even small blood cells (such as platelets) could cross the membrane and contaminate the inside of the probe. Red blood cells would normally not cross the membrane barrier, even if fluid perfusion across the membrane stops. On balance, a pore diameter of 1 to 5 µm is suitable for epicardial and endocardial lesion formation. Where a larger pore diameter is employed, thereby resulting in significant fluid transfer through the porous region, a saline solution having a sodium chloride concentration of about 0.9% weight by volume would be preferred.

With respect to porosity, which represents the volumetric percentage of the outer casing 184 that is composed of pores and not occupied by the casing material, the magnitude of the porosity affects electrical resistance. Low-porosity materials have high electrical resistivity, whereas high-porosity materials have low electrical resistivity. The porosity of the outer casing 184 should be at least 1% for epicardial and endocardial applications employing a 1 to 5 µm pore diameter.

Turning to water absorption characteristics, hydrophilic materials are generally preferable because they possess a greater capacity to provide ionic transfer of RF energy without significant liquid flow through the material.

As illustrated for example in FIG. 21, an exemplary energy transmission assembly 166" includes a base member 168" that carries an electrode 102' and a tissue cooling apparatus 196. The tissue cooling apparatus 196 consists of a wettable fluid retention element 198 that is simply saturated with ionic fluid (such as saline) prior to use, as opposed to having the fluid pumped through the apparatus in the manner described above with reference to FIGS. 19 and 20. The electrode 102' is carried within the fluid retention element 198. The energy transmission assembly 166" illustrated in FIG. 21 may be provided in both bipolar and unipolar implementations.

Suitable materials for the fluid retention element 198 include biocompatible fabrics commonly used for vascular patches (such as woven Dacron®), open cell foam materials, hydrogels, nanoporous balloon materials (with very slow fluid delivery to the surface), and hydrophilic nanoporous materials. The effective electrical resistivity of the fluid retention element 198 when wetted with 0.9% saline (normal saline) should range from about 1 Ω-cm to about 2000 Ω-cm. A preferred resistivity for epicardial and endocardial procedures is about 1000 Ω-cm.

Other variations concern the manner in which the energy transmission assembly is secured to the clamp or other device. For example, the energy transmission assemblies may be permanently secured to a clamp or other device. Also, in any of the unipolar implementations described above, the base member may, if desired, be configured to be secured to both clamp members of a single clamp simultaneously instead on one clamp member.

Surgical Probes

As shown by way of example in FIGS. 22-25, a surgical probe 230 in accordance with a preferred embodiment of a present invention includes a relatively short shaft 232, a shaft distal section 234 and a handle 234. The shaft 232 consists of a hypotube 238, which is either rigid or relatively stiff, and an outer polymer tubing 240 over the hypotube. The handle 236 preferably consists of two molded handle halves and is provided with strain relief element 242. The shaft 232 in the illustrated embodiment may be from 4 inches to 18 inches in length and is preferably 6 inches to 8 inches. The distal section 234, which is preferably either malleable, somewhat flexible or some combination thereof, may be from 1 inch to 10 inches in length and is preferably 2 to 3 inches. With respect to the distal section 234 in the exemplary embodiment, a plurality of electrode assemblies 100, including electrodes 102 (or 102') and power supply lines 104 and 106, are carried on a support structure 118. A tissue cooling apparatus, such as those disclosed in U.S. application Ser. No. 09/761, 981, may be positioned over the electrodes 102 if desired.

As used herein the phrase "relatively stiff" means that the shaft (or distal section or other structural element) is either rigid, malleable, or somewhat flexible. A rigid shall cannot be bent. A malleable shaft is a shaft that can be readily bent by the physician to a desired shape, without springing back when released, so that it will remain in that shape during the surgical procedure. Thus, the stiffness of a malleable shall must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible shafts are preferably formed from stainless steel, while malleable shafts are formed from annealed stainless steel.

One method of quantifying the flexibility of a shall, be it shafts in accordance with the present inventions or the shafts of conventional catheters, is to look at the deflection of the shaft when one end is fixed in cantilever fashion and a force normal to the longitudinal axis of the shaft is applied somewhere between the ends. Such deflection (cr) is expressed as follows:

$$\sigma = WX^2(3L-X)/6EI$$

where:
W is the force applied normal to the longitudinal axis of the shaft,
L is the length of the shaft,
X is the distance between the fixed end of the shaft and the applied force,
E is the modulous of elasticity, and
I is the moment of inertia of the shaft.

When the force is applied to the free end of the shaft, deflection can be expressed as follows:

$$\sigma = WL^3/3EI$$

Assuming that W and L are equal when comparing different shafts, the respective E and I values will determine how much the shafts will bend. In other words, the stiffness of a shaft is a function of the product of E and I. This product is referred to herein as the "bending modulus." E is a property of the material that forms the shaft, while I is a function of shaft geometry, wall thickness, etc. Therefore, a shaft formed from relatively soft material can have the same bending modulus as a shaft formed from relatively hard material, if the moment of inertia of the softer shaft is sufficiently greater than that of the harder shaft.

For example, a relatively stiff 2 inch shaft (either malleable or somewhat flexible) would have a bending modulus of at least approximately 1 lb.-in.$^2$. Preferably, a relatively stiff 2 inch shall will have a bending modulus of between approximately 3 lb.-in.$^2$ and approximately 50 lb.-in.$^2$. By comparison, 2 inch piece of a conventional catheter shaft, which must be flexible enough to travel through veins, typically has bending modulus between approximately 0.1 lb.-in.$^2$ and approximately 0.3 lb.-in.$^2$. It should be noted that the bending modulus ranges discussed here are primarily associated with initial deflection. In other words, the bending modulus ranges are based on the amount of force, applied at and normal to the free end of the longitudinal axis of the cantilevered shaft, that is needed to produce 1 inch of deflection from an at rest (or no deflection) position.

As noted above, the deflection of a shaft depends on the composition of the shaft as well as its moment of inertia. The shaft could be made of elastic material, plastic material, elasto-plastic material or a combination thereof. By designing the shaft to be relatively stiff (and preferably malleable), the surgical tool is better adapted to the constraints encountered during the surgical procedure. The force required to bend a relatively stiff 2 inch long shaft should be in the range of approximately 1.5 lbs. to approximately 12 lbs. By comparison, the force required to bend a 2 inch piece of conventional catheter shall should be between approximately 0.2 lb. to 0.25 lb. Again, such force values concern the amount of force, applied at and normal to the free end of the longitudinal axis of the cantilevered shaft, that is needed to produce 1 inch of deflection from an at rest (or no deflection) position.

Ductile materials are preferable in many applications because such materials can deform plastically before failure due to fracturing. Materials are classified as either ductile or brittle, based upon the percentage of elongation when the fracture occurs. A material with more than 5 percent elongation prior to fracture is generally considered ductile, while a material with less than 5 percent elongation prior to fracture is generally considered brittle. Material ductility can be based on a comparison of the cross sectional area at fracture relative to the original cross area. This characteristic is not dependent on the elastic properties of the material.

Alternatively, the shaft could be a mechanical component similar to shielded (metal spiral wind jacket) conduit or flexible Loc-Line®, which is a linear set of interlocking ball and socket linkages that can have a center lumen. These would be hinge-like segmented sections linearly assembled to make the shaft.

In those instances where a malleable shaft 232 is desired, the hypotube 238 may be a heat treated malleable hypotube. By selectively heat treating certain portions of the hypotube, one section of the hypotube can be made more malleable than the other. The outer tubing 240 may be formed from Pebax® material, polyurethane, or other suitable materials.

As noted above, the distal section 234 can be either somewhat flexible, in that it will conform to a surface against which it is pressed and then spring back to its original shape when removed from the surface, malleable, or some combination thereof. A bending modulus of between 3 lb.-in.$^2$ and 50 lb.-in.$^2$ is preferred. In the exemplary implementation illustrated in FIGS. 22-25, the distal section 234 includes a malleable proximal portion and a flexible distal portion. Although the relative lengths of the portions may vary to suit particular applications, the malleable proximal portion and a flexible distal portion are equal in length in the illustrated embodiment.

The exemplary malleable portion includes a mandrel 242 made of a suitably malleable material, such as annealed stainless steel or beryllium copper, that may be fixed directly within the distal end of the shaft's hypotube 238 and secured by, for example, soldering, spot welding or adhesives. Sufficient space should be provided to allow the power supply lines 104 and 106 and the temperature sensor signal lines 130 to pass. An insulating sleeve 244 is placed over the mandrel 242 to protects the power supply lines 104 and 106 and the temperature sensor signal lines 130. The insulating sleeve 244 is preferably formed from Pebax® material, polyurethane, or other suitable materials. Turning to the flexible portion, a spring member 246, which is preferably either a solid flat wire spring (as shown), a round wire, or a three leaf flat wire Nitinol spring, is connected to the distal end of the mandrel 242 with a crimp tube or other suitable instrumentality. The distal end of the spring member 246 is connected to a tip member 248 by, for example, soldering, spot welding or adhesives. Other spring members, formed from materials such as 17-7 or carpenter's steel, may also be used. The spring member 246 is also enclosed within the insulating sleeve 244. The spring member 246 may be pre-stressed so that the distal tip is pre-bent into a desired shape. Additional details concerning distal sections that have a malleable proximal portion and a flexible distal portion are provided in U.S. application Ser. No. 09/536,095, which is entitled "Loop Structure For Positioning Diagnostic Or Therapeutic Element On The Epicardium Or Other Organ Surface" and incorporated herein by reference.

In an alternative configuration, the distal section 234 may be formed by a hypotube that is simply a continuation of the shaft hypotube 238 covered by a continuation of the outer tubing 240. However, the distal end hypotube can also be a separate element connected to the shaft hypotube 238, if it is desired that the distal end hypotube have different stiffness (or bending) properties than the shaft hypotube. It should also be noted that the distal section 234 may be made malleable from end to end by eliminating the spring member 246 and extending the malleable mandrel 242 to the tip member 248.

Conversely, the distal section 234 may be made flexible from end to end by eliminating the malleable mandrel 242 and extending the spring member 246 from the hypotube 238 to the tip member 248.

With respect to the connection of the electrode assemblies 100 on the exemplary surgical probe 230 illustrated in FIGS. 22-25 to the ESU 134 or other power supply and control device, the power supply lines 104 and 106 and temperature sensor signal lines 130 associated with each electrode 102 pass through the distal section 234 and shaft 232 and are connected to a PC board 250 in the handle 236. The handle also includes a port 252 that is configured to receive a connector cable (not shown) the connects the PC board 250 (and, therefore, the electrode assemblies 100) to the ESU 134 or other power supply and control device.

Although the present inventions have been described in terms of the preferred embodiments above, numerous modifications and/or additions to the above-described preferred embodiments would be readily apparent to one skilled in the art. By way of example, but not limitation, the present electrode assemblies may also be used in conjunction with steerable and non-steerable catheter-type probes. It is intended that the scope of the present inventions extend to all such modifications and/or additions and that the scope of the present inventions is limited solely by the claims set forth below.

What is claimed is:

1. A method of delivering coagulation energy to a patient tissue with an electrode of an electrophysiological device, the method comprising:
   positioning a clamp member of the electrophysiological device relative to the patient tissue, so that an electrode carried by the clamp member contacts the patient tissue; and
   supplying power sufficient to coagulate the tissue to first and second longitudinally spaced locations on the electrode via first and second power supply lines, respectively, such that a percentage of the power supplied to the first location of the electrode is dissipated prior to reaching the second location to which power is applied by the second power supply line,
   wherein the power supplied via the first power supply line to the first location is supplied independently of the power supplied via the second power supply line to the second location.

2. The method according to claim 1, wherein power is simultaneously supplied to the first and second longitudinally spaced locations on the electrode via the first and second power supply lines.

3. The method according to claim 1, wherein the first and second longitudinally spaced locations on the electrode are separated by a distance of about 2 cm to about 8 cm.

4. The method according to claim 1, further comprising supplying power sufficient to coagulate the tissue to a third location on the electrode via a third power supply line.

5. The method according to claim 1, further comprising controlling the power supplied to the first location based on a temperature sensed by a first temperature sensor associated with the electrode, and controlling the power supplied to the second location based on a temperature sensed by a second temperature sensor associated with the electrode.

6. A method of delivering coagulation energy to a patient tissue with an electrophysiological device, the method comprising:
   positioning the electrophysiological device relative to a patient tissue, so that an electrode of the electrophysiological device contacts the patient tissue; and
   supplying power sufficient to coagulate the tissue to first and second longitudinally spaced locations on the electrode via first and second power supply lines, respectively, such that a percentage of the power supplied to the first location of the electrode is dissipated prior to reaching the second location to which power is applied by the second power supply line,
   wherein the power supplied via the first power supply line to the first location is supplied independently of the power supplied via the second power supply line to the second location.

7. The method according to claim 6, further comprising controlling the power supplied to the first location based on a temperature sensed by a first temperature sensor of the electrophysiological device, and controlling the power supplied to the second location based on a temperature sensed by a second temperature sensor of the electrophysiological device.

8. The method according to claim 7, wherein the first and second temperature sensors are coupled with the electrode.

9. The method according to claim 7, wherein the first and second temperature sensors are coupled with a return electrode of the electrophysiological device.

10. The method according to claim 6, wherein power is simultaneously supplied to the first and second longitudinally spaced locations on the electrode via the first and second power supply lines.

11. The method according to claim 6, wherein the first and second longitudinally spaced locations on the electrode are separated by a distance of about 2 cm to about 8 cm.

12. The method according to claim 6, further comprising supplying power sufficient to coagulate the tissue to a third location on the electrode via a third power supply line.

13. A method of delivering coagulation energy to a patient tissue with an electrophysiological device, the method comprising:
   positioning the electrophysiological device relative to a patient tissue, so that an electrode assembly of the electrophysiological device contacts the patient tissue; and
   supplying power sufficient to coagulate the tissue to first and second locations on the electrode assembly via first and second power supply lines, respectively, such that power supplied to the first location of the electrode assembly is diminished prior to reaching the second location to which power is applied by the second power supply line,
   wherein the power supplied via the first power supply line to the first location is supplied independently of the power supplied via the second power supply line to the second location.

14. The method according to claim 13, wherein the first location of the electrode assembly is disposed on a first delivery electrode of the electrode assembly, and the second location of the electrode assembly is disposed on a second delivery electrode of the electrode assembly.

15. The method according to claim 13, further comprising controlling the power supplied to the first location based on a temperature sensed by a first temperature sensor of the electrophysiological device, and controlling the power supplied to the second location based on a temperature sensed by a second temperature sensor of the electrophysiological device.

16. The method according to claim 15, wherein the first and second temperature sensors are coupled with the electrode assembly.

17. The method according to claim 15, wherein the first and second temperature sensors are coupled with a return electrode of the electrophysiological device.

18. The method according to claim 13, wherein power is simultaneously supplied to the first and second locations on the electrode assembly via the first and second power supply lines.

19. The method according to claim 13, wherein the first and second locations on the electrode assembly are separated by a distance of about 2 cm to about 8 cm.

20. The method according to claim 13, further comprising supplying power sufficient to coagulate the tissue to a third location on the electrode assembly via a third power supply line.

* * * * *